United States Patent
Schmitt et al.

(10) Patent No.: US 8,661,904 B2
(45) Date of Patent: Mar. 4, 2014

(54) METHOD FOR INVESTIGATING A STRUCTURE FOR RECEIVING AND/OR CONDUCTING A LIQUID OR SOFT MEDIUM

(75) Inventors: Martin Schmitt, Coburg (DE); Hendrik Faustmann, Coburg (DE); Katrin Schmidt, Steinach (DE); Gerhard Linder, Coburg (DE)

(73) Assignee: Hochschule fuer Angewandten Wissenschafen Fachhochschule Coburg, Coburg (DE)

( * ) Notice: Subject to any disclaimer, the term of this patent is extended or adjusted under 35 U.S.C. 154(b) by 271 days.

(21) Appl. No.: 13/120,012

(22) PCT Filed: Sep. 22, 2009

(86) PCT No.: PCT/EP2009/062265
§ 371 (c)(1),
(2), (4) Date: Apr. 11, 2011

(87) PCT Pub. No.: WO2010/034715
PCT Pub. Date: Apr. 1, 2010

(65) Prior Publication Data
US 2011/0239769 A1    Oct. 6, 2011

(30) Foreign Application Priority Data

Sep. 23, 2008  (DE) .......................... 10 2008 048 557
Sep. 3, 2009   (EP) ................................ 09 169 414
Sep. 15, 2009  (EP) ................................ 09 075 426

(51) Int. Cl.
*G01N 29/04* (2006.01)
*G01F 23/296* (2006.01)

(52) U.S. Cl.
USPC .............................. 73/597; 73/599; 73/290 V (58) Field of Classification Search
USPC ........ 73/290 V, 61.62, 61.63, 61.75, 597, 599
See application file for complete search history.

(56) References Cited

U.S. PATENT DOCUMENTS 4,679,430 A * 7/1987 Scott-Kestin et al. ...... 73/290 V
(Continued)

FOREIGN PATENT DOCUMENTS

CN           101133314 A    2/2008
(Continued)

OTHER PUBLICATIONS

Lindner G. et al. "A Versatile Acoustic Waveguide Sensor for Liquids Based on Multiple Mode Conversion at Solid-Liquid Interfaces", 2006 Proc. IEEE Ultrasonic Symp. 1181-1184.

(Continued)

*Primary Examiner* — John Chapman, Jr.
(74) *Attorney, Agent, or Firm* — Machoff Brennan (57) ABSTRACT

The invention relates to a method for investigating a structure and a structure for receiving and/or conducting a liquid or soft medium, the method comprising the steps of:
a) exciting acoustic waves in the structure by means of at least one transmitter,
b) converting at least a part of the energy associated with the acoustic waves (A) excited in the structure into volume sound waves of the medium,
c) reconverting at least a part of the energy associated with the volume sound waves into acoustic wave energy of the structure thereby generating acoustic waves in the structure,
d) receiving acoustic waves evoked by the transmitter by at least one receiver, and
e) verifying whether a coating is present on a surface of the structure and/or if a coating is present determining properties of the coating by evaluating a signal generated by the receiver upon receipt of acoustic waves evoked by the transmitter and/or verifying whether a level of the medium (5) is below a predetermined value.

22 Claims, 9 Drawing Sheets

(56) References Cited

U.S. PATENT DOCUMENTS

| | | |
|---|---|---|
| 6,192,751 B1 | 2/2001 | Stein et al. |
| 6,420,816 B2 | 7/2002 | Getman et al. |
| 6,684,703 B2 | 2/2004 | Chatellier et al. |
| 7,375,454 B2 | 5/2008 | Takasaki |
| 2002/0162395 A1 | 11/2002 | Chatellier et al. |
| 2008/0240762 A1 | 10/2008 | Casagrande |
| 2008/0240763 A1 | 10/2008 | Casagrande |
| 2009/0229345 A1 | 9/2009 | Van Kesteren |

FOREIGN PATENT DOCUMENTS

| | | |
|---|---|---|
| DE | 36 90 687 C2 | 1/1990 |
| DE | 196 12 925 C1 | 5/1997 |
| DE | 199 61 857 A1 | 6/2001 |
| DE | 11 2005 002 562 | 11/2007 |
| DE | 10 2007 030 566 A1 | 10/2008 |
| EP | 0 372 700 A1 | 6/1990 |
| EP | 0372700 A1 | 6/1990 |
| EP | 0 988 538 B1 | 3/2000 |
| GB | 2192717 A | 1/1988 |
| JP | 2003-525443 A | 8/2003 |
| WO | 2008/034878 A2 | 3/2008 |
| WO | 2008034878 A2 | 3/2008 |

OTHER PUBLICATIONS

Lindner G. "Sensors and actuators based on surface acoustic waves propagating along solid-liquid interfaces" J. Phys. D: Appl. Phys. 41 (2008) 123002 (13 pp).

Faustmann, H. et al. "Acoustic liquid sensor based on Lamb waves on structural materials", Proc. Eurosensors XXII, Dresden, 2008, p. 227-230.

Hauptmann, P. et al. "Application of ultrasonic sensors in the process industry" Meas. Sci. Technol. 13 R73-R83, (2002).

* cited by examiner

METHOD FOR INVESTIGATING A STRUCTURE FOR RECEIVING AND/OR CONDUCTING A LIQUID OR SOFT MEDIUM

BACKGROUND

The invention relates to a method for investigating a structure and to a structure for receiving and/or conducting a liquid or soft medium.

SUMMARY

Non-destructive testing of structures, such as solid substrates, conduits or containers, is of large technical importance. For example, several methods are known for determining properties of layers on solid substrates. However, the known methods are not or only to a limited extent suited for the detection of layers that are deposited on a surface of the structure to which access is not possible or difficult.

It is an object of the invention to provide a more versatile method for investigating a structure.

According to the invention, a method for investigating a structure (in particular for receiving and/or conducting a liquid or soft medium) is provided, comprising the steps of:
a) exciting acoustic waves in the structure by means of at least one transmitter,
b) converting at least a part of the energy associated with the acoustic waves excited in the structure into volume sound waves of the medium,
c) reconverting at least a part of the energy associated with the volume sound waves into acoustic wave energy of the structure thereby generating acoustic waves in the structure,
d) receiving acoustic waves evoked by the transmitter by at least one receiver,
e) verifying whether a coating is present on a surface of the structure and/or—if a coating is present—determining properties of the coating by evaluating a signal generated by the receiver upon receipt of acoustic waves evoked by the transmitter, and/or
f) verifying whether a level of the medium is below a predetermined value by evaluating a signal generated by the receiver upon receipt of acoustic waves evoked by the transmitter.

For example, a part of the acoustic waves received by the receiver can be waves that are transmitted directly from the transmitter to the receiver via a portion of the structure, e.g. in the form of Lamb or Lamb-Rayleigh waves propagating in the structure. In the case of Lamb waves or Lamb-Rayleigh-waves the displacement of opposite surfaces of the structure excited by the transmitter is correlated such that, in particular, the amplitude and/or the phases of the displacement movement of the (e.g. inner and outer) surfaces of the structure are interrelated.

For example, the acoustic waves excited in the structure will be mainly or only Lamb waves if the thickness of the structure is substantially smaller than the wavelength of the excited waves. However, as set forth above, also a transition type of Lamb waves and Rayleigh waves can be used, i.e. the thickness of the structure can be of the same order of magnitude as the wave length of the excited waves. In that case there can still be a correlation between the displacement movement of the opposite surfaces of the structure (e.g. of the outer atomic layers of the surfaces of the structure).

Further, the waves received by the receiver can be waves that are generated by mode conversion, i.e. waves are excited in the structure (in particular in the form of Lamb waves or Lamb-Rayleigh waves) and at least a portion of these acoustic waves is converted into sound waves in the medium (for example a liquid) interfacing the structure, which e.g. is confined in an interior space of the structure. The sound waves in the medium may then be reflected from another portion of the structure towards the receiver and are reconverted into (surface) waves (Lamb or Lamb-Rayleigh waves) in the structure which propagate in the structure towards the receiver. In other words, the acoustic waves excited in the structure, the volume sound waves in the medium created by conversion of the waves in the structure and the waves propagating in the structure created by re-conversion of volume sound waves are referred to as waves "evoked by the transmitter".

It is also possible that repeated mode conversion occurs, i.e. a first volume sound wave created by mode conversion of a first (surface) acoustic wave in the waveguide side structure is reconverted into a second acoustic wave in the waveguide side structure. Then, the second acoustic wave is converted into a second volume sound wave in the medium, wherein interference between the second volume sound wave and a reflected component of the first volume sound wave can occur, wherein this interference creates areas of high and low sound wave energy which may be used to sample certain areas of the medium and/or the coating. Of course, more than two conversion and reconversion processes are possible.

In order to excite Lamb or Lamb-Rayleigh waves in the structure acoustic waves are excited in the structure having a suited frequency, the required frequency being chosen from a frequency range depending on the thickness of the structure in which the acoustic waves shall be induced.

For example, the method according to the invention comprises arranging the transmitter and the receiver on the structure, wherein the structure may be a part of an arbitrary existing technical device, such as a conduit for piping a liquid or soft medium or a receptacle for such a medium. A "soft material" comprises, for example, a (e.g. biological) tissue or a gel, i.e. in particular a material having similar velocities of sound as a liquid and in which mainly longitudinal acoustic modes are excited.

In other words, the method according to the invention permits to test (e.g. liquid filled) technical structures by arranging (e.g. attaching using, for example, epoxy or another adhesive, e.g. an ultrasonic adhesive) an acoustic transmitter and an acoustic receiver to the structure and evaluating the signal generated by the receiver upon receipt of acoustic waves. In particular, the coating can comprise a slurry or an organic (biological) substance such as mud. In another example, the coating comprises lime. Also, the coating might be a photo resist which is spin coated on a substrate, wherein the transmitter might be arranged on a rotating plate for arranging the substrate (e.g. a semi-conductor wafer).

In particular, the conduit has a circular or a rectangular cross section, wherein the transmitter and the receiver might be arranged on different portions of a side wall of the conduit. These existing conducts or containers do not necessarily have to comprise or consist of a piezoelectric material as the transmitter is configured to excite waves also in non-piezoelectric materials such as metal or glass.

Further more, the transmitter and the receiver are arranged on a surface of the structure which faces away from the surface on which the coating is arranged or the presence of the coating is to be verified, i.e. the transmitter and the receiver are arranged on an external surface of the structure to be tested. As mentioned above, the structure to be investigated may have an inner surface interfacing with a liquid or a soft medium (or a gas) and an outer surface facing away from the inner surface. The method according to the invention, for example, comprises arranging the transmitter and the receiver on the outer surface of the structure.

Further, the transmitter and/or the receiver might be equipped with means for detachably fixing the transmitter and/or the receiver to the structure. The transmitter and/or the receiver may be interdigital piezo-electric transducers. However, the term "transmitter" is not restricted to a piezo-electric transducer. Other embodiments of the invention comprise a transmitter in the form of a (e.g. pulsed) laser that excites the acoustic wave in the side structure of the waveguide based on thermoelastic effects. Also, a wedge ("wedge converter") could be used (in particular in combination with a piezo-electric transducer) to excite the acoustic waves or a comb-like vibrator ("comb converter"). Of course different transmitter types could also be used in combination.

In another example of the invention, the transmitter and the receiver are not attached supplementary to an existing technical structure but are arranged on a side structure of an acoustic waveguide, i.e. the "structure" is the side structure of the acoustic waveguide. The acoustic waveguide may be coupled to a technical device, which is the actual device to be investigated, such as a conduit for piping a liquid or a container for receiving a liquid or a soft medium. A change of the coating on an inner surface of the waveguide side structure which interfaces the interior space of the waveguide corresponds to a change of a coating (e.g. a change of the thickness of the coating) on a part of the coupled technical device such that a coating on an internal surface of the technical device can be monitored.

"Monitoring" the coating in particular means that a first signal generated by the receiver at a first point in time and a second signal generated by the receiver at a second point in time are evaluated. Of course, more than two signals generated at more than two points in time can be evaluated. In particular, the monitoring can be carried out simultaneously (or quasi-simultaneously).

For example, evaluating the signal generated by the receiver comprises evaluating the amplitude and the time response of the signal. For example, the transmitter excites pulsed acoustic waves in the structure having a certain propagation time from the transmitter to the receiver (depending on the path between the transmitter and the receiver they take). Changes of the properties of a surface of the structure (e.g. an interface between the structure and a medium) influence the propagation time of the waves in the structure. Thus, evaluating changes in the propagation time allow the determination of properties of a coating or a verification whether or not a coating is present at the interface.

Further more, the mode conversion, i.e. the conversion of acoustic waves in the structure into sound waves in a medium interfacing the structure, depends on the presence of a coating and the properties of the coating, respectively. Thus, a first signal may be generated by the receiver upon receiving acoustic waves directly transmitted from the transmitter via the structure and a second signal may be generated due to acoustic sound waves in the medium induced by the acoustic waves in the structure and travelling towards to receiver, wherein both the first and the second signal depend on the properties of a coating at the interface (and of course on the presence or absence of such a coating).

For example, evaluating the signal generated by the receiver comprises comparing the results of the evaluation with pre-determined values. In particular, the amplitude and/or the time response of the receiver signal are compared to pre-determined amplitude and/or the time response values. The pre-determined values may have been generated using a similar structure as the structure to be investigated (or the structure to be investigated itself), wherein a coating was deposited whose properties or at least some of its properties were known. Also, the pre-determined values could be determined using a similar structure (or the structure to be investigated itself) without any coating to obtain reference values for a non-coated structure. In other words, the transmitter-receiver arrangement is calibrated. Variations from the calibration values indicate the presence of a coating or permit to determine a change of properties of the coating.

According to another embodiment of the invention, the transmitter and the receiver are arranged along the propagation direction of the acoustic waves excited in the structure.

Also in this case, the structure may be an existing structure of a technical device, wherein the transmitter and the receiver are supplementary arranged on that structure (for example during operation of the technical device).

For example, the structure to be investigated has a longitudinal axis (e.g. the structure is formed as a tube or any other symmetric structure) or (more generally speaking) extends mainly longitudinally, wherein both the transmitter and the receiver are arranged in a row along the longitudinal axis and along the main extension direction of the structure, respectively.

A further receiver might be arranged on the structure, in particular with a distance to a connecting line between the transmitter and the receiver. The further (second) receiver thus may detect sound waves excited in the media due to mode conversion before those sound waves are registered by the (first) receiver (which is arranged in a row with the transmitter along the propagation direction).

The transmitter and the receiver may also be arranged on a first portion of the structure and the further receiver is arranged on a second portion of the structure, the second portion extending opposite to the first portion. In addition, a further (second) receiver may be arranged in such a way that the distance between the transmitter and the further receiver and the distance between the (first) receiver and the further (second) receiver is essentially identical.

However, the further receiver may also be arranged at a different location, for example directly opposite to the receiver such that a connecting line between the receiver and the further receiver extends essentially perpendicular to the propagation direction of the acoustic waves excited in the structure. For example, the transmitter, the transceiver, the further receiver and a longitudinal axis of the structure lie in the same plane.

For example, the structure to be investigated may comprise a first and a second plate, the two plates being arranged opposite to one another, wherein the transmitter and the receiver are arranged on the first plate and the further receiver is arranged on the second plate. The two plates may be connected in order to form a closed interior space of the structure. For example, the two plates are portions of a conduit or a container having a rectangular cross section. However, it is also possible that the two plates are not connected or that they are connected only in such a way that acoustic waves excited in one of the plates are not transmitted to the other plate.

According to another embodiment of the invention, the transmitter and the receiver are arranged in such a way that the connecting line between the transmitter and the receiver crosses an interior space of the structure. In other words, the transmitter and the receiver are not arranged on the same side of the structure but, for example, on opposite sides of the structure. Again, a further receiver might be arranged on the structure.

More particularly, the further receiver may be disposed on the structure in such a way that the transmitter is positioned with a distance to a connecting line between the receiver and the further receiver. In other words, the transmitter is positioned in such a way with respect to the two receivers that both receivers will receive sound waves excited in a medium located in an interior space of the structure, wherein the sound waves will be reconverted into acoustic waves travelling in the structure before being registered by the receivers.

In particular, the distance between the transmitter and the receiver and the distance between the transmitter and the further receiver may be essentially identical, i.e. the transmitter is positioned in the middle between the two receivers. Using that configuration more detailed information regarding the presence or properties of a coating may be obtained as the signal generated by the receivers may reflect changes of both the mode conversion effect and the propagation of acoustic waves (for example in the form of Lamb waves) in the structure and/or the coating.

Also, the signal of the receivers is influenced by the properties, i.e. the presence and/or the properties of a coating of an (inner) surface of the (first) portion of the structure where the transmitter is located and by the properties of the (inner) surface of the (second) portion where the two receivers are located such that the presence and/or the properties of a coating on both the first and the second portion can be determined.

Further more, local variations of a coating could be determined with this arrangement. For example, if a coating is present in the region of the receiver that has different properties (e.g. a different thickness) then a coating in the region of the further receiver the signal at the (first) receiver will be different from the signal at the further (second) receiver. Of course, more than two receivers could be used to get more detailed spatial information. Also, more than one transmitter could be applied.

It is another object of the invention to provide a structure for receiving and/or conducting a liquid or soft medium which is more reliable or which can be used for investigating a hollow element for receiving and/or conducting a liquid or soft medium.

According to the invention, the structure comprises
a) an inner surface interfacing a liquid or soft medium,
b) a transmitter for exciting acoustic waves in the structure,
c) an interface between the structure and the medium, where at least a part of the energy associated with the acoustic waves in the structure is converted into volume sound waves of the medium,
d) an interface between the structure and the medium, where at least a part of the energy associated with the volume sound waves is reconverted into acoustic wave energy of the structure thereby generating acoustic waves in the structure,
e) a receiver for receiving acoustic waves evoked by the transmitter, wherein
f) evaluation means are provided for evaluating a signal generated by the receiver upon receipt of acoustic waves evoked by the transmitter in order to verify whether a coating is present between the inner surface of the structure and the medium and/or if a coating is present for determining properties of the coating and/or for verifying whether a level of the medium is below a predetermined value.

The evaluation means might for example be implemented as an electrical circuit, e.g. in the form of a microchip. The microchip may be arranged on the side structure of the waveguide. However, it is also conceivable that the evaluation means are not realized in form of an integrated circuit but comprise a measurement device arranged separately to the waveguide. In particular, the measurement device (such as an oscilloscope or a computer) is connected to the receiver in order to register the electrical receiver signals. Further, a computer program can be used to evaluate the receiver signals registered by the measurement device.

According to an embodiment of the invention, the structure is a side structure of an acoustic waveguide, the side structure delimiting an interior space filled with the medium.

For example, the structure comprises coupling means for coupling the acoustic waveguide to a hollow element at least partially filled with a medium (e.g. a liquid or a gas). In particular, the coupling means permit the acoustic waveguide to be coupled to a hollow element in the form of a container and/or a conduit for piping a liquid or a soft medium. In particular, the coupling means permit the waveguide to be coupled to the hollow element along the longitudinal axis of the hollow element and the waveguide. For example, the coupling means comprise a flange, which for example is located at one face side of the waveguide. However, the coupling means could—as an alternative or additionally—comprise other elements such as clamping means or a thread, i.e. means that permit a form fit and/or a force fit between the device and the hollow element.

Thus, the device according to the invention can be coupled to an existing structure, wherein the development of a coating on a surface of the structure can be determined indirectly by determining changes of a coating on an inner surface of the acoustic waveguide.

As similarly set forth above, the transmitter and the receiver may be arranged in a row along the propagation direction of the acoustic waves excited in the structure. Also, a further receiver can be arranged with a distance to the connecting line between the transmitter and the receiver.

Furthermore, the further receiver may be arranged in such a way that the connecting line between the transmitter and the further receiver crosses the interior space of the waveguide. In particular, the further receiver is arranged in the middle between the transmitter and the receiver. According to that arrangement, the receiver (arranged along with the transmitter) will receive both acoustic waves which are transmitted directly via the structure and waves which result from sound waves in a medium and which are reconverted into acoustic waves of the structure.

The further receiver will mainly detect sound waves excited in the medium due to mode conversion. Thus, two sets of signals (generated by the receiver and the further receiver, respectively) are available for evaluation in order to determine properties of a coating. For example, it could be determined from the receiver signals whether a coating is present only on the portion of the side structure where the transmitter and the receiver are positioned or whether a coating is also present on the portion of the side structure where the further receiver is arranged. Also, inhomogeneities of a coating may influence the signals at the two receivers differently such that for example a local distribution of mating properties may be deduced from the two sets of receiver signals.

In another configuration, the two receivers are arranged on the same portion of the side structure. Further, the structure can comprise two plates arranged opposite to one another, wherein the transmitter and the receiver are arranged on an outer surface of the plates similarly as discussed above with respect to the method according to the invention.

BRIEF DESCRIPTION OF THE DRAWINGS

Embodiments of the invention will be described in more detail hereinafter with reference to the drawings, in which.

DETAILED DESCRIPTION OF THE DRAWINGS

Figure 1:
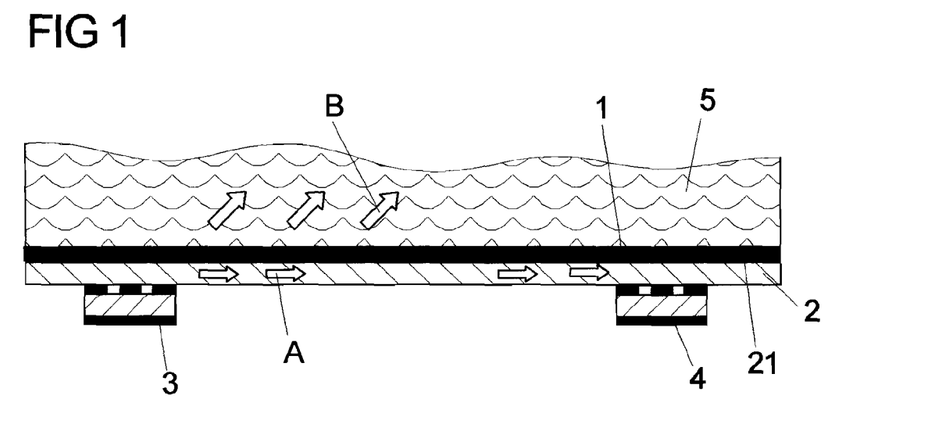
FIG. 1 illustrates the method according to a first embodiment of the invention, wherein a coating between a structure and a medium is identified.

According to FIG. 1, a homogeneous coating in the form of a material layer 1 is present on a first side 21 of a structure for receiving and/or conducting a liquid or soft medium in the form of a solid substrate 2 interfacing a liquid 5. In order to detect properties or the presence of layer 1 a transmitter 3 in the form of an interdigital transducer and an interdigital transducer operated as receiver 4 are arranged on a second side 22 facing away from the first side 21 of the substrate 2.

The transmitter 3 excites acoustic Lamb waves (indicated by arrows A) in the substrate 2. At least a portion of the lamb waves A are conveyed to the receiver 4 directly through the substrate 2, wherein the amplitude and the propagation time (i.e. the time the Lamb wave needs to travel from the transmitter 3 to the receiver 4) depends on the properties of the first surface 21, i.e. in particular on the properties of the layer 1. Thus, changes of the layer properties result in changes of the signal generated by the receiver 4 upon receipt of acoustic waves. Also, properties of the signal generated by receiver 4 (such as amplitude and time response) may be compared to predetermined or theoretical values such that not only changes of the properties of layer 1 can be detected but also absolute values of the properties such as the layer thickness or local variations of the layer thickness.

Due to the presence of the liquid 5 mode conversion occurs, i.e. at least a part of the Lamb waves A induced in the substrate 2 are converted into volume sound waves B in the liquid 5. As both the direct transmission of acoustic waves from the transmitter 3 to the receiver 4 via substrate 2 and the mode conversion depends on the properties of the coating layer 1 more detailed information about layer properties may be obtained. For example, information about the thickness and the material of the layer as well as about the extension or adhesion of the layer may be deduced from the receiver signal.

Figure 2:
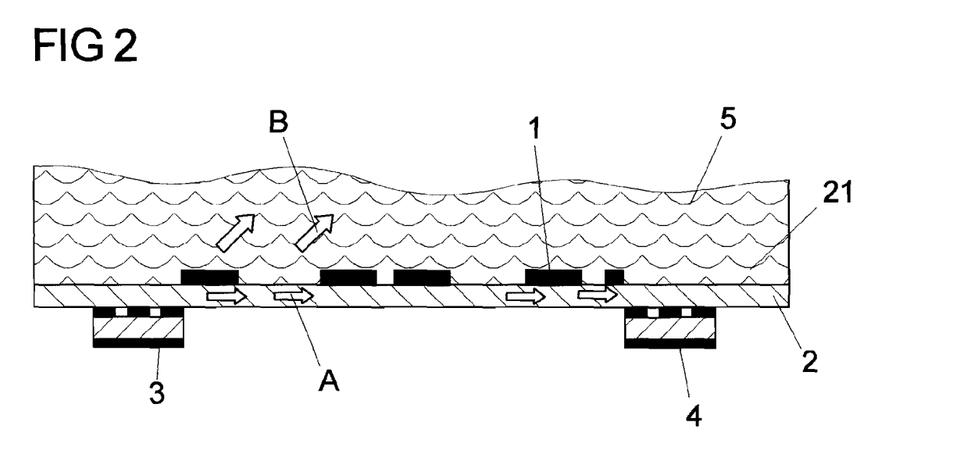
FIG. 2 further illustrates a method according to the first embodiment of the invention, wherein an inhomogeneous coating is detected.

FIG. 2 shows the arrangement of FIG. 1, wherein, however, an inhomogeneous layer 1 is present at the first side 21 of the substrate 2, wherein the method according to the invention also permits to identify such inhomogeneous layers. In particular, the mode conversion is influenced by the spatial density distribution of layer 1 such that sound waves are induced in the liquid 3 under different Rayleigh angles depending on whether or not a layer is present (or generally depending on a variation of the thickness of the layer). Thus, a superposition of different sound waves (associated with different Rayleigh angles) will arrive at the receiver 4. It is thus possible to obtain information on the spatial distribution of the layer thickness by a deconvolution of the receiver signal.

Figure 3:
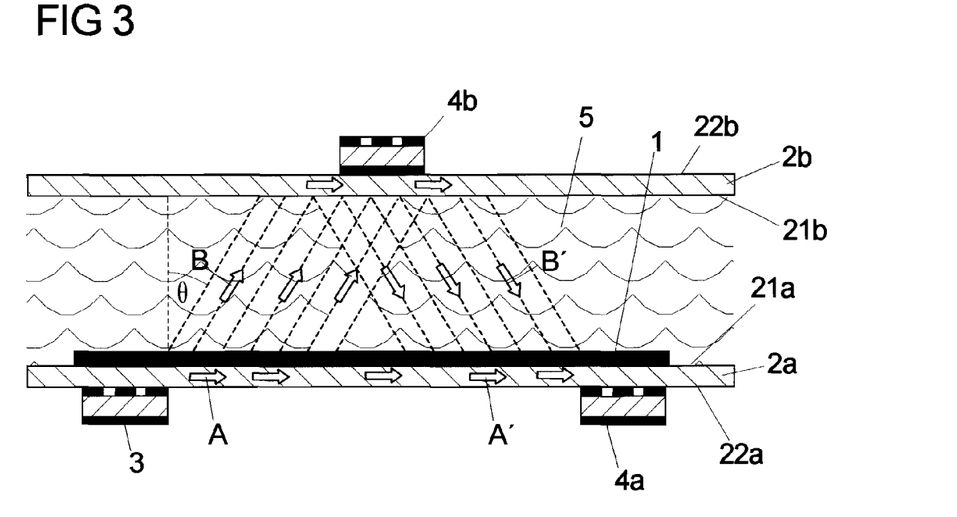
FIG. 3 illustrates the method according to a second embodiment of the invention, wherein a transmitter and a first receiver are arranged at a first portion of a structure and a second receiver is arranged at a second portion of the structure.

Referring to FIG. 3, another embodiment of the invention is illustrated, wherein the structure to be investigated comprises a first portion in the form of a (plate-like) first substrate 2a and a second portion in the form of substrate 2b. For example, the substrates 2a, 2b form part of a side structure of an acoustic waveguide, the substrates 2a, 2b delimiting an interior space of the waveguide where the medium 5 is located. Similarly to the previous Figures, a transmitter 3 and a receiver 4a is arranged along the propagation direction of the Lamb waves A at an outer side 22a of the first substrate 2a. In particular, the acoustic waveguide comprising the substrates 2a, 2b may have means for coupling the waveguide to a hollow element (not shown) such that a liquid flows through both the hollow element and the waveguide.

A further receiver 4b is arranged with a distance to a connecting line between the transmitter 3 and the receiver 4a, i.e. the further receiver 4b is arranged with a distance to the first substrate 2a. More particularly, the transmitter 3 and the receiver 4a are arranged on the first substrate 2a and the further receiver 4b is arranged on the substrate 2b. Both substrate 2a and 2b are formed as plates and arranged opposite and parallel to one another.

The substrates 2a, 2b may be connected, for example, by additional side wall structures in order to form a closed interior space in which a liquid 5 is located. For example, these connecting portions of the structure may be formed of a different material than the substrates 2a, 2b. However, it is also possible that the structure to be investigated is integrally formed (at least in the area of the transmitter and the receivers) such that an essentially continuous side wall is formed on which the transmitter and the receivers are arranged. In particular, the transmitter and the first receiver 4a are arranged on a first section of that side wall and a second receiver 4b is arranged on another section of that side wall, which in particular extends opposite to the first section of the side wall.

According to the example of FIG. 3, the further receiver 4b is arranged in such a way that the distance between the further receiver 4b and the transmitter and the distance between the further receiver 4b and the receiver 4a are essentially identical. However, other arrangements are possible. For example, the further receiver 4b could be arranged closer to the receiver 4a such that the distance between the further receiver 4b and the receiver 4a would be smaller than the distance between the further receiver 4b and the transmitter 3.

As indicated in FIG. 3, a part of the acoustic Lamb waves A induced in the first substrate 2a are converted into sound waves B in the liquid 5, wherein the sound waves B are "emitted" under the Rayleigh angle θ. A part of the sound waves B are reflected by an inner surface 21b of the second substrate 2b (indicated by arrows B') towards the (first) receiver 4a. Another part of the sound waves B are reconverted into acoustic Lamb waves in the second substrate 2b, which are then detected by the further (second) receiver 4b. Similarly, the reflected sound waves B' are reconverted into acoustic Lamb waves in the first substrate (indicated by arrows A') which are then detected by receiver 4a.

The conversion and reconversion of Lamb waves into sound waves and vice versa depends on the interfaces between the two substrates 2a, 2b and the liquid 5, i.e. on the presence and/or properties of a coating on the inner surfaces 21a, 21b such that the signal generated by the receivers 4a and 4b reflects the coating properties. Thus, properties and the presence of a coating on the inner surfaces 21a, 21b can be deduced from the signals generated by the receivers 4a, 4b.

Figure 4:
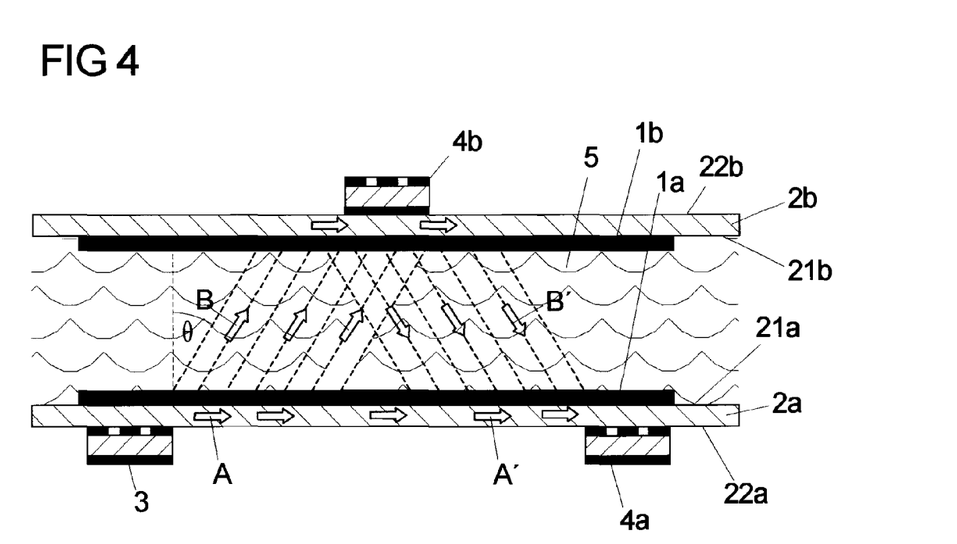
FIG. 4 further illustrates the method according to the second embodiment of the invention, wherein coatings on the first and the second portion of the structure are detected.
Figure 5:
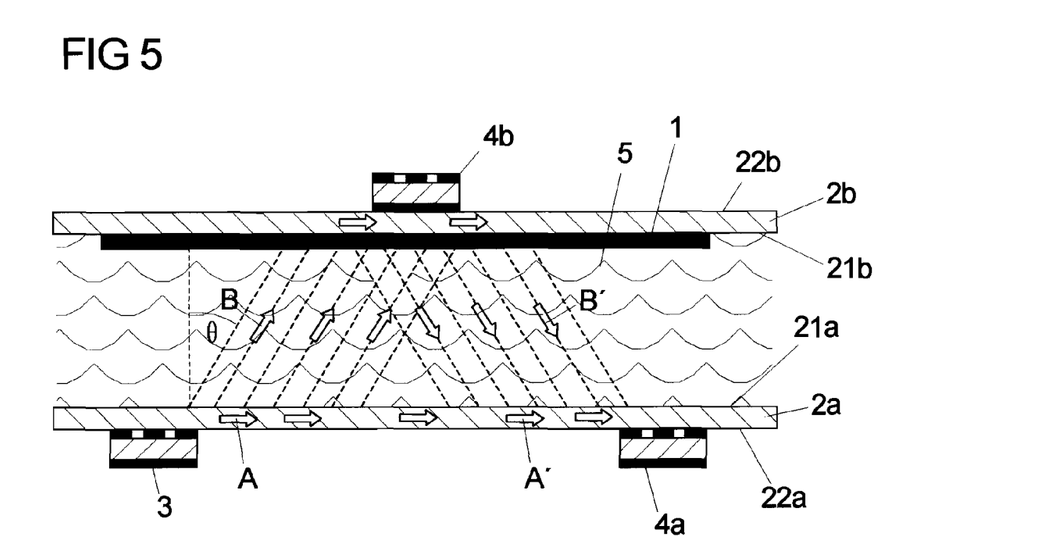
FIG. 5 further illustrates the method according to the second embodiment of the invention, wherein a coating on the second portion is detected.

For example, it is possible to determine properties (such as a thickness) of coatings on both inner surfaces 21a, 21b as shown in FIGS. 4 and 5, wherein according to FIG. 4 a coating 1a, 1b is present on both surfaces 21a, 21b and according to FIG. 5 a coating 1 is present at the (upper) inner surface 21b, only.

Figure 6:
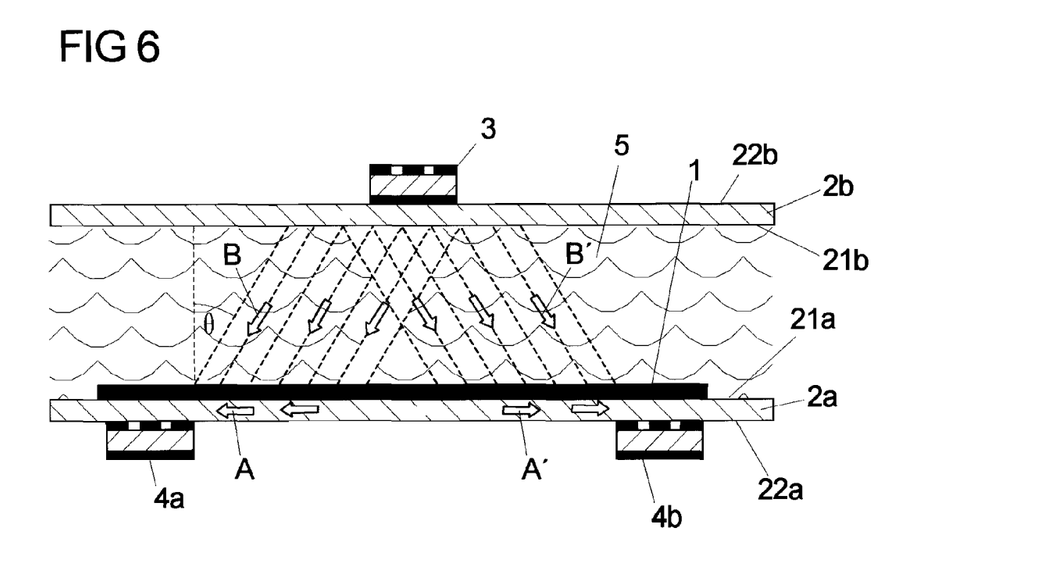
FIG. 6 further illustrates the method according to a third embodiment of the invention, wherein a coating on the first portion of the structure is detected.

Another arrangement for carrying out the method according to the invention is illustrated in FIG. 6. Similar to FIGS. 3 to 5, one transmitter and two receivers are used. However, the two receivers 4a, 4b are both arranged on the first substrate 2a, wherein the transmitter 3 is arranged on the second substrate 2b. In other words, the transmitter 3 is arranged in such a way that a connecting line between the transmitter and the receiver 4a or the receiver 4b crosses the interior space filled with the liquid 5 of the structure.

As in the previous examples, the transmitter 3 will excite Lamb waves in the substrate 2b which are converted at least partially into sound waves B, B' in the liquid 5. In the example shown in FIG. 6, the transmitter 3 is arranged in the middle between the two receivers 4a, 4b, i.e. the distance between the receiver and the first receiver 4a and the second receiver 4b is essentially equal. In particular, the transmitter is positioned in such a way that the sound waves B, B' (which are emitted under the Rayleigh angle θ) are emitted toward the receivers 4a, 4b. However, other positions for the transmitter and/or the two receivers 4a, 4b are of course conceivable.

The sound waves B, B' arriving at the first substrate 2a are reconverted into Lamb waves A, A' which travel to the first and the second receiver 4a, 4b, respectively. Again, the signals generated by receivers 4a, 4b upon receipt of the Lamb waves A, A' depend on the properties of the inner surfaces 21a, 21b of the substrates 2a, 2b, i.e. on the properties and/or presence of a coating on these interfaces. Therefore, properties of a coating can be derived from the receiver signals.

To derive properties of a coating the interface between the substrates 2a, 2b may be simulated, the simulation containing different unknown parameters related to the coating which are to be determined from values extracted from the receiver signals (such as values related to the amplitude and the time response of the signals).

Figure 7:
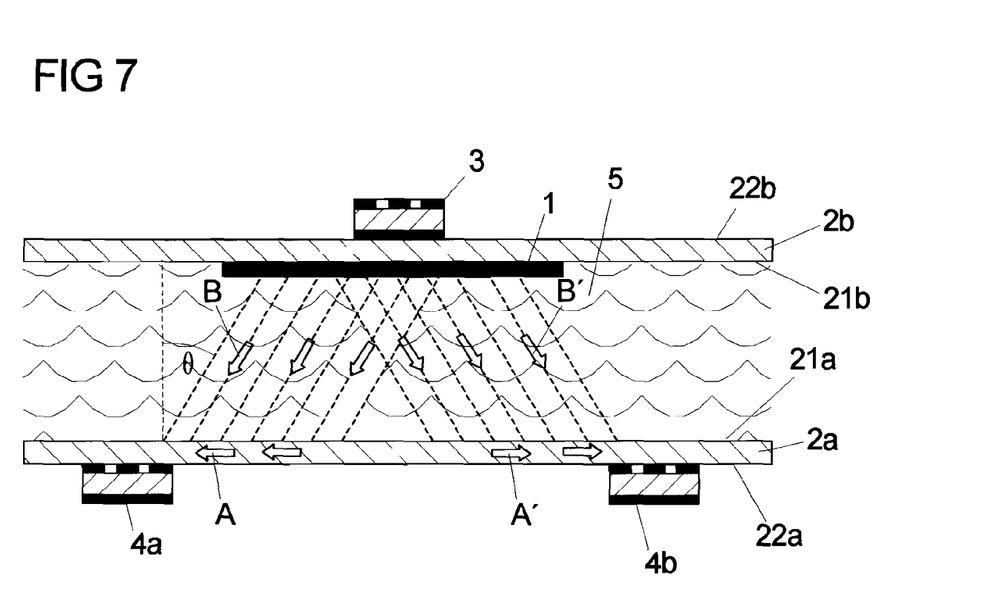
FIG. 7 illustrates the method according to the third embodiment of the invention, wherein inhomogeneous coatings are detected on the first and the second portion of the structure.
Figure 8:
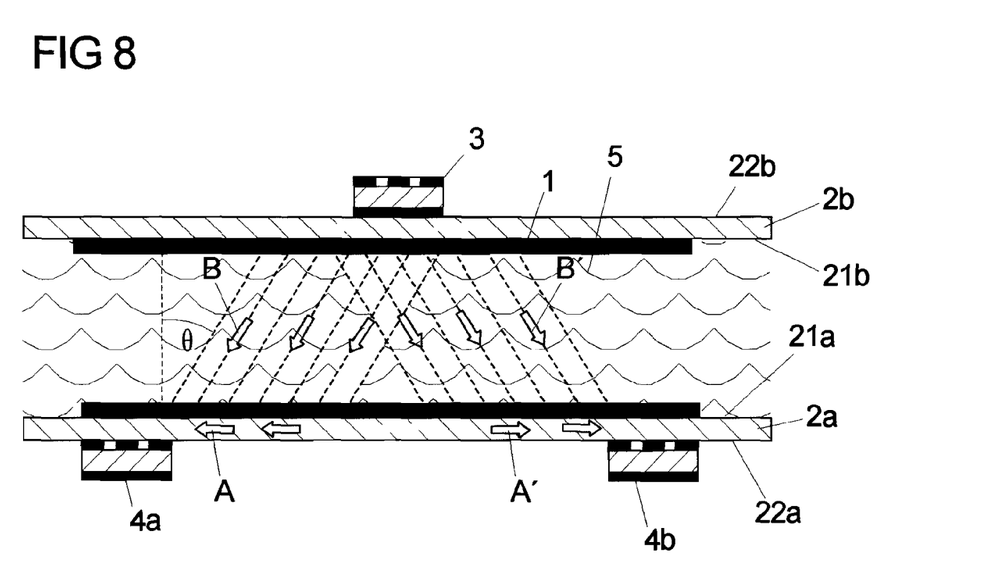
FIG. 8 illustrates a method according to the third embodiment of the invention, wherein coatings at two portions of a structure are detected.
Figure 9:
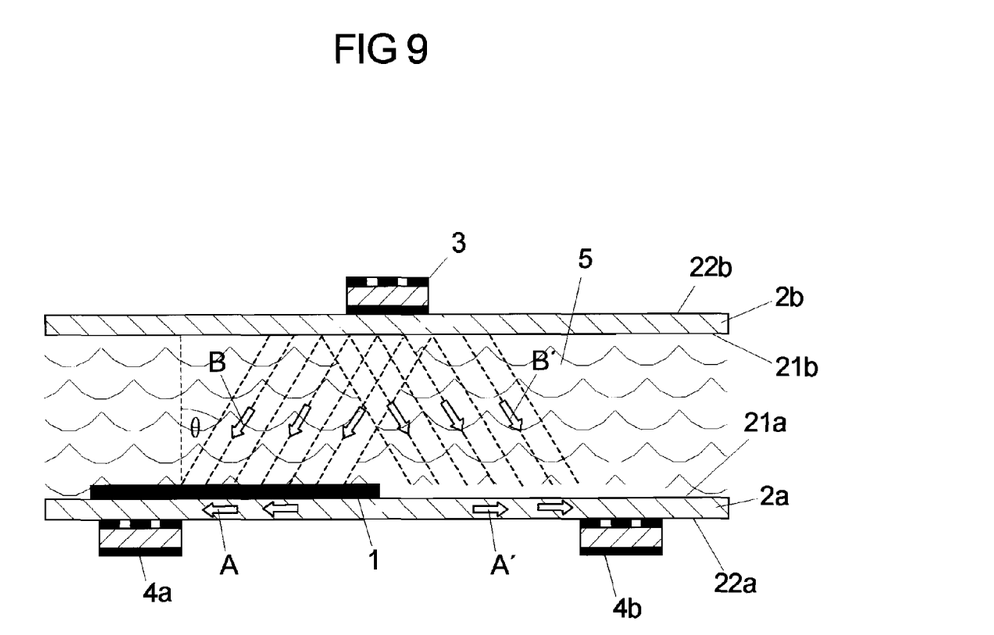
FIG. 9 further illustrates the third embodiment of the invention, wherein an inhomogeneous coating is detected on the first portion.

For example, a three phase model could be used simulating the first substrate, a coating and the liquid, wherein certain properties are assumed to be known (for example material parameters of the substrate, the coating and the liquid) and other parameters are unknown and are to be determined (such as e.g. the thickness of the coating or in particular a thickness function depending on the position on the substrate). Further, more complicated simulations could be used which for example allow to determine properties of inhomogeneous coatings on both inner surfaces 21a, 21b as shown in FIGS. 7 to 9.

Further, receiver signals can be determined for different frequencies, i.e. a first set of receiver signals is determined at a first frequency of Lamb waves in the substrate 2a excited by the transmitter and a second set of signals is registered at a second frequency of Lamb waves in the substrate 2b. Of course, more than two frequencies could be used in order to be able to determine a larger number of unknown parameters of the coating.

Figure 10:
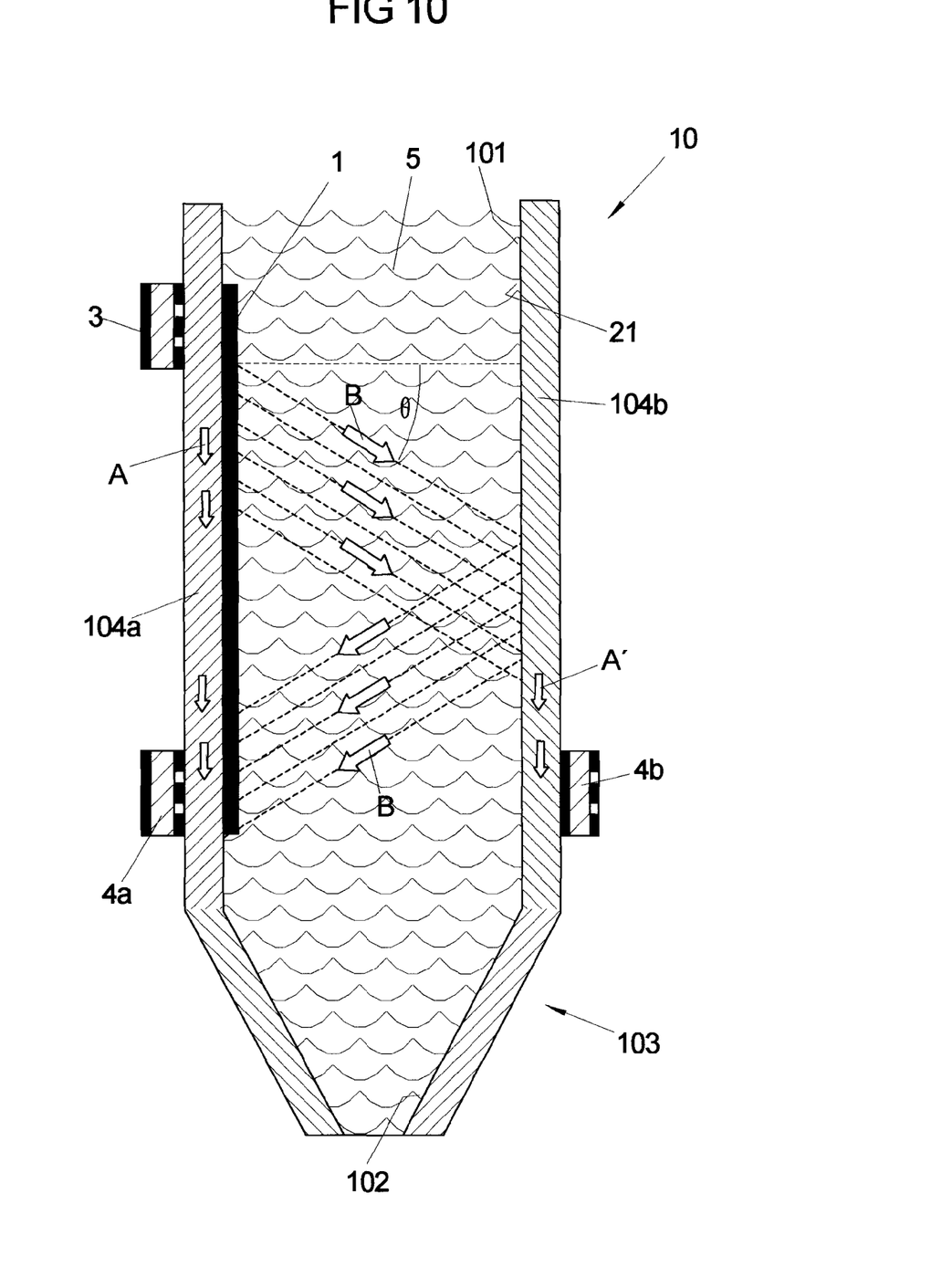
FIG. 10 illustrates the method according to a fourth embodiment of the invention, wherein a transmitter-receiver arrangement is provided at a receptacle for a liquid medium.
Figure 11:
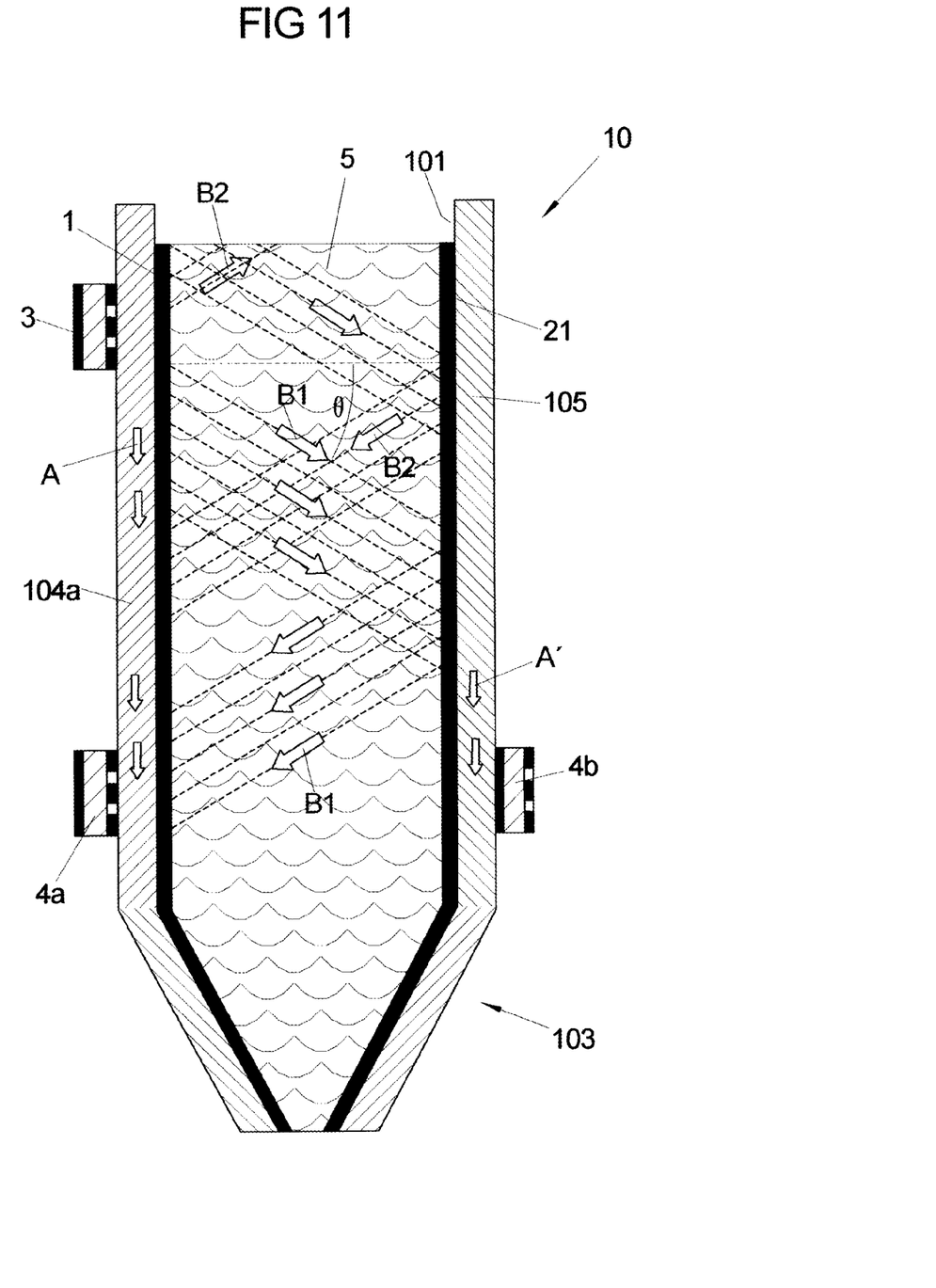
FIG. 11 further illustrates the method according to a fourth embodiment of the invention, wherein a liquid level is determined.
Figure 12:
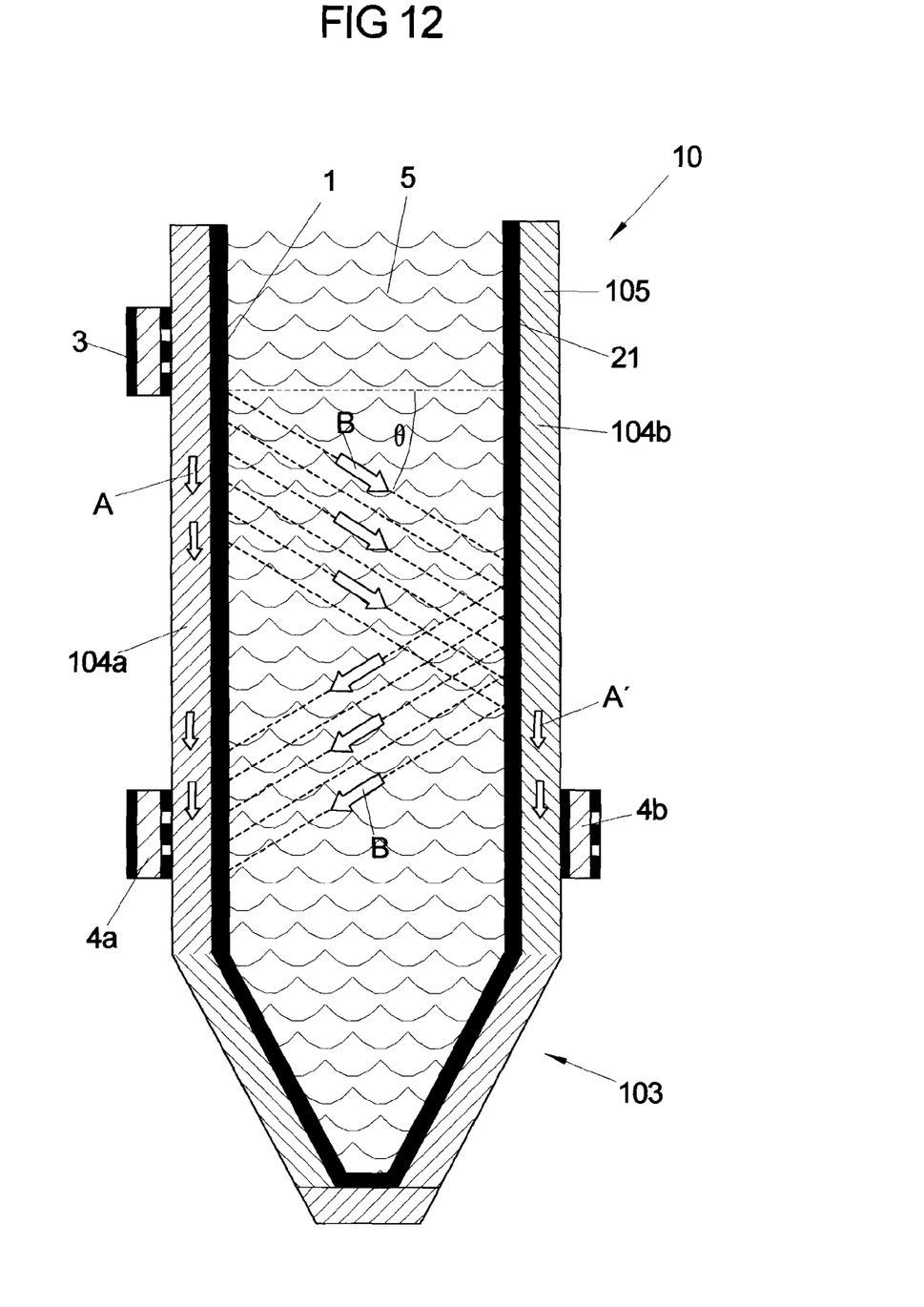
FIG. 12 illustrates a modification of the fourth embodiment.
Figure 13:
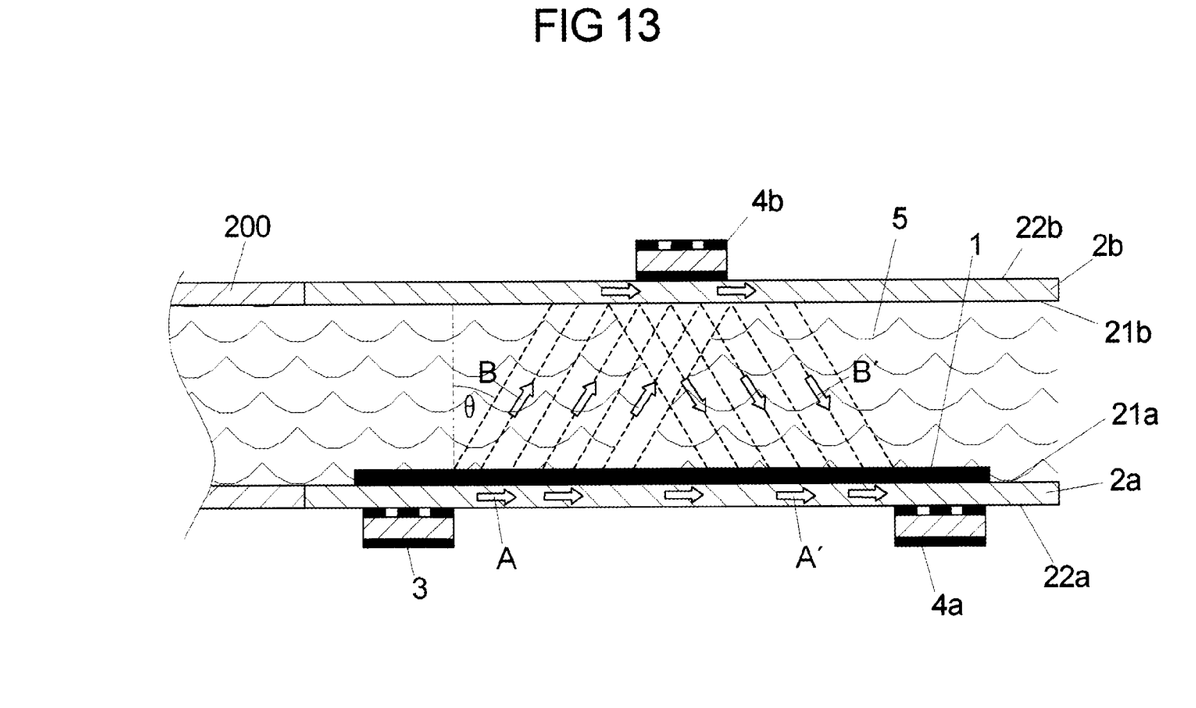
FIG. 13 illustrates a hollow element as a technical device connected to the acoustic wave guide.

A further embodiment of the invention is illustrated in FIGS. 10 to 12. A transmitter-receiver arrangement is arranged at a container (receptacle 10) for receiving a liquid 5. The receptacle may be a test tube or a vessel used in a dialysis device.

In the example of FIGS. 10 and 11, the receptacle 10 comprises a first opening 101 and a second opening 102 arranged near an ending 103 of the receptacle opposite to opening 101. The ending 103 forms a taper towards opening 102.

A transmitter 3 and a first receiver 4a are arranged on a first portion 104a of a side wall of receptacle 10. Further, a second receiver 4b is arranged on an opposite portion 104b of the side wall. As in the previous examples, the transmitter 3 induces Lamb waves A in the structure, i.e. in the first portion 104a of receptacle 10, the Lamb waves being at least partially converted into sound waves B in the liquid 5. The sound waves B in turn are reconverted into Lamb waves A' in the second portion 104b of receptacle 10. The Lamb waves A' in the second portion 104b of receptacle 10 are detected by the second receiver 4b.

Further, another part of the sound waves B is reflected at the second portion 104b towards the first receiver 4a such that the reflected portion B of the sound waves is registered by receiver 4a after reconversion into Lamb waves in the first portion 104a in the area of the first receiver 4a.

Similarly to the previously discussed embodiments, the receiver signals permit to determine properties and/or the presence of a coating 1 located at an inner surface 21 of receptacle 10. In the example according to FIGS. 10 and 11, the two receivers 4a, 4b are arranged opposite in such a way that a connecting line between the two receivers is perpendicular to both side wall portions 104a, 104b and a longitudinal axis (not shown) of receptacle 10, respectively. However, other arrangements of the receivers 4a, 4b are conceivable, for example the second receiver 4b could be positioned in the middle between transmitter and the first receiver 4a such that the distance between the receiver to the transmitter and the first receiver, respectively, are essentially equal.

Another application of the invention is illustrated in FIG. 11, wherein the arrangement corresponds to FIG. 10. In particular, the transmitter 3 is arranged in the area of opening 101 or at least in the area of an ending portion 105 of receptacle 10. This configuration allows to determine the level of the liquid 5 in the receptacle 10, i.e. in particular, it may be monitored if the liquid level drops below a certain level.

For example, if the liquid level is above the height position (measured along the longitudinal axis of receptacle 10) of transmitter 3, i.e. for example that the liquid level is above a line that is perpendicular to the longitudinal axis of receptacle 10 and which intersects the transmitter 3, Lamb waves excited in the first portion 104a of receptacle 10 are induced by transmitter 3 which are converted into first and second sound waves $B_1$, $B_2$ propagating in the liquid 5. The sound waves $B_2$ are emitted in a direction towards the (upper) ending 105

(comprising the opening 101) of the receptacle, whereas the other sound waves B₁ are emitted under a direction inclined towards the other ending 103 of the receptacle 10. Both, sound waves B₁ and B₂, are reflected by the inner surface of receptacle 10 such that after (for example multiple) reflections at the inner surface of the receptacle the waves B₁ and B₂ arrive at receivers 4a and 4b.

If the liquid level drops below a certain level depending on the position of transmitter 3 no sound waves will be emitted in a direction towards the first ending 105 anymore such that the signal at the receivers 4a, 4b will change. Thus, from the receiver signals, in particular from a change of the signals, the level of liquid 5 in the receptacle 10 can be derived. Further, more than one transmitter could be used to be able to determine the position of the liquid level more accurately.

FIG. 12 shows a receptacle similar to FIGS. 10 and 11. One ending 105 comprises the opening 101 for receipt of a medium (a liquid or a soft medium such as a tissue) and in contrast to FIGS. 10 and 11 a closed end 103 opposite to opening 101 is provided. For example, the receptacle 10 of FIG. 12 is a test tube for testing biological or chemical samples.

It is noted that elements of the previously described devices could also be used in combination. For example, the liquid level detection described with respect to FIG. 11 could also be used with a closed receptacle as shown in FIG. 12.

The invention claimed is:

1. A method for investigating a structure having an inner surface interfacing a liquid or soft medium, comprising the steps of:
   a) exciting acoustic waves in the structure by means of at least one transmitter,
   b) converting at least a part of the energy associated with the acoustic waves excited in the structure into volume sound waves of the medium,
   c) reconverting at least a part of the energy associated with the volume sound waves into acoustic wave energy of the structure thereby generating acoustic waves in the structure,
   d) receiving acoustic waves evoked by the transmitter by at least one receiver, and
   e) verifying whether a coating is present between the inner surface of the structure and the medium and/or if a coating is present determining properties of the coating by evaluating a signal generated by the receiver upon receipt of acoustic waves evoked by the transmitter,
wherein:
step e) comprises evaluating a first and a second receiver signal, wherein the first signal is generated by the receiver upon receipt of acoustic waves transmitted directly from the transmitter to the receiver via the structure and the second signal is generated by the receiver due to acoustic sound waves in the medium which were induced by the acoustic waves in the structure and which travel towards the receiver, wherein the structure is a tube-like acoustic wave guide and the transmitter and receiver are arranged on the structure along a line extending parallel to a longitudinal axis of the acoustic wave guide.

2. The method as claimed in claim 1, wherein the frequency of the waves excited in the structure is such that the excited waves are Lamb waves or Lamb-Rayleigh waves.

3. The method as claimed in claim 1, wherein the method comprises arranging the transmitter and the receiver on the structure.

4. The method as claimed in claim 3, wherein the transmitter and the receiver are arranged on a surface of the structure which faces away from the inner surface of the structure.

5. The method as claimed in claim 3, wherein the method comprising arranging the transmitter and the receiver on an outer surface of the structure, the outer surface facing away from a medium.

6. The method as claimed in claim 1, wherein the structure is a container at least partially filled with a medium.

7. The method as claimed in claim 5, wherein the structure is a conduit for piping a medium.

8. The method as claimed in claim 1, wherein the structure is a side structure of an acoustic waveguide which delimits an interior space of the waveguide, wherein the transmitter and the receiver are arranged on the side structure, and the method further comprises coupling the acoustic waveguide to a technical device.

9. The method as claimed in claim 1, wherein evaluating the signal generated by the receiver comprises evaluating the amplitude and the time response of the signal and/or comparing the results of the evaluation with predetermined values.

10. The method as claimed in claim 1, a further receiver is arranged with a distance to a connecting line between the transmitter and the receiver.

11. The method as claimed in claim 1, further comprising verifying whether a level of the medium is below a predetermined value by evaluating a signal generated by the receiver upon receipt of acoustic waves evoked by the transmitter.

12. A structure for receiving and/or conducting a liquid or soft medium, comprising:
   a) an inner surface interfacing a liquid or soft medium,
   b) a transmitter for exciting acoustic waves in the structure,
   c) an interface between the structure and the medium, where at least a part of the energy associated with the acoustic waves in the structure is converted into volume sound waves of the medium,
   d) an interface between the structure and the medium, where at least a part of the energy associated with the volume sound waves is reconverted into acoustic wave energy of the structure thereby generating acoustic waves in the structure,
   e) a receiver for receiving acoustic waves evoked by the transmitter,
   f) evaluation means configured and constructed for evaluating a signal generated by the receiver upon receipt of acoustic waves evoked by the transmitter and for verifying whether a coating is present between the inner surface of the structure and the medium and/or if a coating is present for determining properties of the coating,
wherein
the evaluation means are configured to evaluate a first and a second receiver signal, wherein the first signal is generated by the receiver upon receipt of acoustic waves transmitted directly from the transmitter to the receiver via the structure and the second signal is generated by the receiver due to acoustic sound waves in the medium which were induced by the acoustic waves in the structure and which travel towards the receiver, wherein the structure is a tube-like acoustic wave guide and the transmitter and receiver are arranged on the structure along a line extending parallel to a longitudinal axis of the acoustic wave guide.

13. The structure as claimed in claim 12, wherein the structure is a side structure of an acoustic waveguide, the side structure delimiting an interior space of the waveguide filled with the medium.

14. The structure as claimed in claim 13, further comprising coupling means for coupling the acoustic waveguide to a hollow element at least partially filled with a medium.

15. The structure as claimed in claim 14, wherein the coupling means permit the acoustic waveguide to be coupled to a hollow element in the form of a container and/or a conduit for piping a liquid or a soft medium.

16. The structure as claimed in claim 13, wherein a further receiver is arranged with a distance to a connecting line between the transmitter and the receiver.

17. The structure as claimed in claim 12, wherein a further receiver is arranged in such a way that the transmitter is positioned with a distance to a connecting line between the receiver and the further receiver.

18. The structure as claimed in claim 17, wherein the distance between the transmitter and the receiver and the distance between the transmitter and the further receiver is essentially identical.

19. The structure as claimed in claim 12, wherein the structure is a hollow cylinder comprising an opening for filling in the medium, the opening being arranged in an ending of the cylinder and the transmitter being arranged adjacent to the opening.

20. The structure as claimed in claim 12, wherein the evaluation means is further configured and constructed for verifying a level of the medium is below a predetermined value.

21. A method for investigating a structure having an inner surface interfacing a liquid or soft medium, comprising the steps of:
 a) exciting acoustic waves in the structure by means of at least one transmitter,
 b) converting at least a part of the energy associated with the acoustic waves excited in the structure into volume sound waves of the medium,
 c) reconverting at least a part of the energy associated with the volume sound waves into acoustic wave energy of the structure thereby generating acoustic waves in the structure,
 d) receiving acoustic waves evoked by the transmitter by at least one receiver, and
 e) verifying whether a level of the medium is below a predetermined value by evaluating a signal generated by the receiver upon receipt of acoustic waves evoked by the transmitter,
wherein:
step e) comprises evaluating a first and a second receiver signal, and the first signal is generated by the receiver upon receipt of acoustic waves transmitted directly from the transmitter to the receiver via the structure and the second signal is generated by the receiver due to acoustic sound waves in the medium which were induced by the acoustic waves in the structure and which travel towards the receiver, and the structure is a tube-like acoustic wave guide and the transmitter and receiver are arranged on the structure along a line extending parallel to a longitudinal axis of the acoustic wave guide.

22. A structure for receiving and/or conducting a liquid or soft medium, comprising:
 a) an inner surface interfacing a liquid or soft medium,
 b) a transmitter for exciting acoustic waves in the structure,
 c) an interface between the structure and the medium, where at least a part of the energy associated with the acoustic waves in the structure is converted into volume sound waves of the medium,
 d) an interface between the structure and the medium, where at least a part of the energy associated with the volume sound waves is reconverted into acoustic wave energy of the structure thereby generating acoustic waves in the structure,
 e) a receiver for receiving acoustic waves evoked by the transmitter,
 f) evaluation means configured and constructed for evaluating a signal generated by the receiver upon receipt of acoustic waves evoked by the transmitter or for verifying for verifying whether a level of the medium is below a predetermined value,
wherein:
the evaluation means are configured to evaluate a first and a second receiver signal, wherein the first signal is generated by the receiver upon receipt of acoustic waves transmitted directly from the transmitter to the receiver via the structure and the second signal is generated by the receiver due to acoustic sound waves in the medium which were induced by the acoustic waves in the structure and which travel towards the receiver, wherein the structure is a tube-like acoustic wave guide and the transmitter and receiver are arranged on the structure along a line extending parallel to a longitudinal axis of the acoustic wave guide.

* * * * *

UNITED STATES PATENT AND TRADEMARK OFFICE
CERTIFICATE OF CORRECTION

PATENT NO. : 8,661,904 B2
APPLICATION NO. : 13/120012
DATED : March 4, 2014
INVENTOR(S) : Schmitt et al.

It is certified that error appears in the above-identified patent and that said Letters Patent is hereby corrected as shown below:

On the Title Page, in Item (73), under "Assignee", in Column 1, Lines 1-3,
delete "Hochschule fuer Angewandten Wissenschafen Fachhochschule Coburg, Coburg (DE)"
and insert -- Hochschule fuer Angewandte Wissenschaften Fachhochschule Coburg, Coburg (DE) --,
therefor.

On the Title Page, in Item (74), under "Attorney, Agent, or Firm", in Column 2, Line 1,
delete "Machoff Brennan" and insert -- Maschoff Brennan --, therefor.

Signed and Sealed this
Third Day of June, 2014

Michelle K. Lee
*Deputy Director of the United States Patent and Trademark Office*

UNITED STATES PATENT AND TRADEMARK OFFICE
CERTIFICATE OF CORRECTION

PATENT NO.       : 8,661,904 B2                                                   Page 1 of 1
APPLICATION NO. : 13/120012
DATED            : March 4, 2014
INVENTOR(S)      : Schmitt et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 290 days.

Signed and Sealed this

Twenty-ninth Day of September, 2015

Michelle K. Lee
*Director of the United States Patent and Trademark Office*